United States Patent

Omatsu et al.

[11] Patent Number: 5,932,761
[45] Date of Patent: Aug. 3, 1999

[54] PROCESS FOR PRODUCING BRANCHED ALDEHYDES

[75] Inventors: Toshihiro Omatsu, Ichikawa; Masahiko Kitayama, Nakajo-machi; Takashi Onishi, Hasaki-machi, all of Japan

[73] Assignee: Kuraray Co., Ltd., Kurashiki, Japan

[21] Appl. No.: 09/045,772

[22] Filed: Mar. 23, 1998

[30] Foreign Application Priority Data

Mar. 24, 1997 [JP] Japan .................................. 9-088868
Aug. 26, 1997 [JP] Japan .................................. 9-244784

[51] Int. Cl.$^6$ ........................... C07C 67/38; C07C 67/36
[52] U.S. Cl. ..................... 560/233; 560/231; 560/175; 560/176; 560/177; 560/178
[58] Field of Search .................... 560/231, 233, 560/175, 176, 178, 177

[56] References Cited

U.S. PATENT DOCUMENTS

| | | | |
|---|---|---|---|
| 3,168,553 | 2/1965 | Slaugh et al. | 560/233 |
| 3,239,566 | 3/1966 | Slaugh et al. | 568/454 |
| 3,239,569 | 3/1966 | Slaugh et al. | 568/909 |
| 3,239,571 | 3/1966 | Slaugh et al. | 568/909 |
| 3,732,287 | 5/1973 | Himmele et al. | 560/112 |
| 3,840,589 | 10/1974 | Himmele et al. | 560/238 |
| 3,917,661 | 11/1975 | Pruett et al. | 554/120 |
| 4,871,880 | 10/1989 | Omatsu et al. | 568/454 |
| 5,414,138 | 5/1995 | Omatsu et al. | 568/454 |
| 5,684,167 | 11/1997 | Omatsu et al. | 549/475 |

*Primary Examiner*—Samuel Barts
*Assistant Examiner*—Rosalynd Keys
*Attorney, Agent, or Firm*—Oblon, Spivak, McClelland, Maier & Neustadt, P.C.

[57] ABSTRACT

It is provided a process for industrially advantageously producing a branched aldehyde represented by the formula;

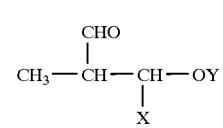

(1)

[wherein Y represents an acyl group of two or more carbon atoms; and X represents an acyloxymethyl group represented by —CH$_2$OY' (where Y' represents an acyl group of two or more carbon atoms), cyano group or an alkoxycarbonyl group] which is useful as an intermediate for pharmaceuticals and agricultural chemicals, comprising subjecting an olefinic compound represented by the following formula;

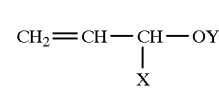

(2)

(wherein Y and X are the same as defined above), to the reaction with hydrogen and carbon monoxide in the presence of a rhodium compound and a tertiary organic phosphorus compound with an electronic parameter (υ-value) of 2080 to 2090 cm$^{-1}$ or with a steric parameter (θ-value) of 150 to 180°.

4 Claims, No Drawings

PROCESS FOR PRODUCING BRANCHED ALDEHYDES

BACKGROUND OF THE INVENTION

1. Field of the Invention

The present invention relates to a process for producing a branched aldehyde represented by the following formula (1);

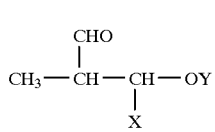
(1)

wherein Y represents an acyl group of two or more carbon atoms; and X represents an acyloxymethyl group represented by —CH$_2$OY' (wherein Y' represents an acyl group of two or more carbon atoms), cyano group or an alkoxycarbonyl group. The branched aldehyde produced by the process of the present invention is useful as an intermediate for phamaceuticals and agricultural chemicals. For example, the branched aldehyde produced by the process of the present invention can be converted into an α, β-unsaturated aldehyde represented by the formula

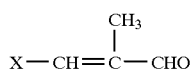

wherein X is the same as defined above, which unsaturated aldehyde is useful as an intermediate for vitamin As [see Pure & Appl. Chem., 63, 45(1991); British Patent No. 1168639; Japanese Patent Application Publication No. Sho 60-9493, etc.] and zeatin, a plant hormone [see U.S. Pat. No. 4,361,702].

2. Related Art of the Invention

Processes for producing 1,2-diacetoxy-3-formylbutane, one of the branched aldehyde represented by the above formula (1), have been known, which comprises hydroformylation of 3,4-diacetoxy-1-butene in the presence of rhodium compounds (see U.S. Pat. No. 3,732,287 and German Patent Application Laid-open No. 2039078).

The U.S. Pat. No. 3,732,287 discloses that 1,2-diacetoxy-3-formylbutane can be produced in good yield through hydroformylation at an elevated temperature and an elevated pressure. The patent also discloses that the reaction temperature is preferably 60 to 120° C., more preferably 80 to 105° C. The patent further describes that the reaction pressure is generally 300 to 1200 atm., preferably 500 to 700 atm.

The German Patent Application Laid-open No. 2039078 discloses, in the Example 1, that 3,4-diacetoxy-1-butene was converted, by the hydroformylation at 600 atm. and 100° C. using a rhodium catalyst, to a mixture of 2000 g of 2-methyl-3,4-diacetoxybutanal (identical with 1,2-diacetoxy-3-formylbutane) and 1700 g of 4,5-diacetoxypentanal.

As described in the German Patent Application Laid-open No. 2039078, 3,4-diacetoxy-1-butene is a compound with an olefinic carbon-carbon double bond at a terminal of the molecule, so the hydroformylation of the compound generally gives a mixture of 4,5-diacetoxypentanal, a linear aldehyde, and 1,2-diacetoxy-3-formylbutane, a branched aldehyde.

The U.S. Pat. No. 3,732,287 and the German Patent Application Laid-open No. 2039078 both require to carry out the hydroformylation at least at a pressure as high as 300 atm in order to produce 1,2-diacetory-3-formylbutane in good yield. Therefore, the methods disclosed in these documents require high cost for equipment durable at such high pressure as described above in order to carry out the method in an industrial scale, and consequently, the production cost of 1,2-diacetoxy-3-formylbutane is disadvantageously high.

The present inventors have made attempts to reduce the pressure for the hydroformylation of 1,3-diacetoxy-1-butene for industrial advantages, and found that the selectivity to 1,2-diacetoxy-3-formylbutane was lowered. For example, the ratio of 1,2-diacetoxy-3-formylbutane and 4,5-diacetoxypentanal was 40/60 (former/latter) in the resulting product when the hydroformylation was carried out at 100 atm. and 80° C. using a rhodium carbonyl complex as a catalyst.

SUMMARY OF THE INVENTION

It is an object of the present invention to provide a process for industrially advantageously producing a branched aldehyde represented by the formula (1), including 1,2-diacetoxy-3-formylbutane, which comprises the hydroformylation of an olefinic compound including 3,4-diacetoxy-1-butene, as represented by the formula (2);

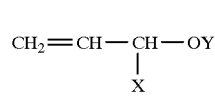
(2)

wherein Y and X are independently the same as described above, using a rhodium compound as the catalyst, in which process the hydroformylation can be carried out at a lower pressure than that of the conventional method, without the reduction of selectivity to the branched aldehyde.

The object of the present invention can be achieved by a process described hereinbelow.

More specifically, the present invention provides a process for producing a branched aldehyde represented by the formula (1);

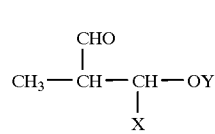
(1)

[wherein Y represents an acyl group of two or more carbon atoms; and X represents an acyloxymethyl group represented by —CH$_2$OY' (where Y' represents an acyl group of two or more carbon atoms), cyano group or an alkoxycarbonyl group], comprising subjecting an olefinic compound represented by the following formula (2);

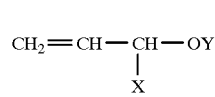
(2)

wherein Y and X are the same as described above, to the reaction with hydrogen and carbon monoxide in the presence of a rhodium compound and a tertiary organic phosphorus compound with an electronic parameter (υ-value) of 2080 to 2090 cm$^{-1}$ or with a steric parameter (θ-value) of 150 to 180°.

DETAILED DESCRIPTION OF THE INVENTION

The present invention is described in more detail.

The acyl group of two or more carbon atoms represented by Y and the acyl group of two or more carbon atoms represented by Y' in case that the X is an acyloxy group represented by —CH$_2$Y', include, for example, acetyl group, propionyl group, butyryl group, isobutyryl group, valeryl group, isovaleryl group, pivaloyl group, hexanoyl group and heptanoyl group. Among them, the acyl group of seven or less carbon atoms is preferable. These acyl groups may have a substituent such as fluorine atom, which does not inhibit the hydroformylation of the olefinic compound represented by the formula (2).

The alkoxycarbonyl group represented by X includes, for example, methoxycarbonyl group, ethoxycarbonyl group, propoxycarbonyl group, isopropoxycarbonyl group, n-butoxycarbonyl group, t-butoxycarbonyl group, pentoxycarbonyl group, hexyloxycarbonyl group and benzyloxycarbonyl group.

Examples of the olefinic compound represented by the formula (2) include 3,4-diacetoxy-1-butene, 3,4-dipropionyloxy-1-butene, 3,4-divaleroxy-1-butene, 3,4-diisovaleroxy-1-butene, 1-cyano-2-propenyl acetate, 1-cyano-2-propenyl propanoate, 1-cyano-2-propenyl benzoate, 1-methoxycarbonyl-2-propenyl acetate, 1-methoxycarbonyl-2-propenyl propanoate, 1-ethoxycarbonyl-2-propenyl benzoate, 1-t-butoxycarbonyl-2-propenyl acetate and 1-benzyloxycarbonyl-2-propenyl acetate. Among them, acetates such as 3,4-diacetoxy-1-butane, 1-cyano-2-propenyl acetate, 1-methoxycarbonyl-2-propenyl acetate, 1-t-butoxycarbonyl-2-propenyl acetate and 1-benzyloxycarbonyl-2-propenyl acetate are preferable in order to carry out the process of the present invention in an industrial scale.

The olefinic compound represented by the formula (2) can be produced, for example, by the following known processes;
(i) a process in which 1,3-butadrene is oxidized in the presence of a carboxylic acid (see U.S. Pat. No. 3,723,510);
(ii) a process in which acrolein is converted into the corresponding cyanohydrin and the resulting cyanohydrin is esterified with a carboxylic anhydride such as acetic anhydride, propionic anhydride and butanoic anhydride (see German Patent Application Laid-open No. 3634151); and
(iii) a process in which acrolein is converted into the corresponding cyanohydrin, the resulting cyanohydrin is solvolyzedwith analcohol such as methanol, ethanol, propanol, isopropanol and butanol, and the resulting product is esterified with a carboxylic anhydride such as acetic anhydride, propionic anhydride and butanoic anhydride (see German Patent Application Laid-open No. 3634151).

The rhodium compound used in the present invention includes a rhodium compound which has a catalytic activity for hydroformylation or which can be converted to a compound having a catalytic activity for hydroformylation under the reaction conditions. Examples of the rhodium compound include, for example, $Rh_4(CO)_{12}$, $Rh_6(CO)_{16}$, Rh(acac)(CO)$_2$, rhodium oxide, rhodium chloride, rhodium acetylacetonate and rhodium acetate.

The rhodium compound is used at a concentration, in a reaction solution, of preferably 0.01 to 1 mg atom/liter, more preferably 0.01 to 0.25 mg atom/liter, on a rhodium atom basis from the viewpoint of productivity and production cost.

The tertiary organic phosphorus compound used in the present invention is required to have an electronic parameter (υ-value) of 2080 to 2090 cm$^{-1}$ or a steric parameter(θ-value) of 150 to 180°.

The above two parameters are those defined according to the teachings of a literature [C. A. Tolman, Chem. Rev., 177, 313(1977)]; the electronic parameter is defined as the frequency of the Al infrared absorption spectrum of the CO in an Ni(CO)$_3$L (wherein "L" is a ligand containing phosphorous) measured in dichloromethane; and the steric parameter is defined as the apex angle of a cylindrical cone, centered at a position of 2.28 angstroms from the center of the phosphorus atom, which just touches the Van der Waals radii of the atoms most externally present in the groups bonded to the phosphorus atom.

The tertiary organic phosphorus compound used in the present invention can be represented by the following formula;

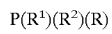

P(R$^1$)(R$^2$)(R$^3$)

wherein R$^1$, R$^2$ and R$^3$ are independently an aryl group, an aryloxy group, an alkyl group, an alkoxy group, a cycloalkyl group or a cycloalkyloxy group, which may have a substituent.

The aryl group represented by R$^1$, R$^2$ and R$^3$ includes, for example, tolyl group, xylyl group and t-butylphenyl group; and the aryloxy group represented by R$^1$, R$^2$ and R$^3$ includes, for example, phenoxy group, o-t-butylphenoxy group and o-ethylphenoxy group. The alkyl group represented by R$^1$, R$^2$ and R$^3$ includes, for example, n-butyl group and n-octyl group, and the alkoxy group represented by R$^1$, R$^2$ and R$^3$ includes, for example, n-octyloxy group. In addition, the cycloalkyl group represented by R$^1$, R$^2$ and R$^3$ includes, for example, cyclohexyl group; and the cycloalkyloxy group represented by R$^1$, R$^2$ and R$^3$ includes, for example, cyclohexyloxy group. R$^1$, R$^2$ and R$^3$ each may have a substituent which does not inhibit the hydroformylation.

Examples of the tertiary organic phosphorus compound include phosphites such as triphenyl phosphite, tris(2-methylphenyl) phosphite, tris(2-ethylphenyl) phosphite, tris(2-isopropylphenyl) phosphite, tris(2-phenylphenyl) phosphite, tris(2,6-dimethylphenyl) phosphite, tris(2-t-butylphenyl) phosphite, tris(2-t-butyl-5-methylphenyl) phosphite, tris(2,4-di-t-butylphenyl) phosphite, di(2-methylphenyl)(2-t-butylphenyl) phosphite and di(2-t-butylphenyl)(2-methylphenyl) phosphite; and phosphines such as tricyclohexylphosphine.

If a tertiary organic phosphorus compound with both the electronic parameter and steric parameter outside the range described above, such as triphenylphosphine (υ: 2068.9 cm$^{-1}$, θ: 145°), tri-o-tolylphosphine (υ: 2066.6 cm$^{-1}$, θ: 194°) and tri-n-butyl phosphite (υ: 2076 cm$^{-1}$, θ: 109°), is used, a linear aldehyde, a by-product, represented by the formula (3);

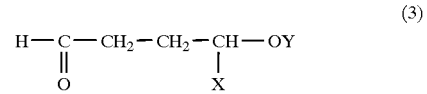

(3)

wherein X and Y are the same as described above, is formed in a considerable amount, so that the selectivity to the branched aldehyde represented by the formula (1) is reduced.

In the present invention, the tertiary organic phosphorus compound with an electronic parameter of 2050 to 2090 cm$^{-1}$ and a steric parameter of 150 to 180°, such as tris(2-phenylphenyl) phosphite (υ: 2085.0 cm$^{-1}$, θ: 152°), tris(2-t-butylphenyl) phosphite (υ: 2086.1 cm$^{-1}$, θ: 175°), tris(2-t-butyl-5-methylphenyl) phosphite (2085.6 cm$^{-1}$, θ: 175°), tris(2,4-di-t-butylphenyl) phosphite ($\upsilon$: 2085.6 cm$^{-1}$, $\theta$: 175°) and tricyclohexylphosphine ($\upsilon$:2056.4 cm$^{-1}$, $\theta$: 170°), is preferable, because a higher reaction rate and selectivity to the branched aldehyde represented by the formula (1) can be attained.

The tertiary organic phosphorus compound is generally used at a concentration of 1 to 20 millimoles/liter in a reaction solution. The tertially organic phosphorous compound is preferably used at a concentration of 2 to 10 millimoles/liter in a reaction solution, because the higher reaction rate and selectivity to the branched aldehyde represented by the formula (1) can be attained.

The tertiary organic phosphorus compound may be used singly or in combination.

In the hydroformylation according to the present invention, tertiary amines such as triethylamine and triethanolamine; and basic substances including carbonates or hydrogencarbonates such as sodium hydrogencarbonate, sodium carbonate and potassium carbonate can be used.

The hydroformylation according to the present invention is carried out generally at a temperature within a range of 20 to 150° C., preferably at a temperature within a range of 40 to 120° C. When the reaction temperature is less than 20° C., the reaction rate is reduced. On the other hand, when the reaction temperature is higher than 150° C., the selectivity to the branched aldehyde represented by the formula (1) tends to be reduced.

The molar ratio of hydrogen and carbon monoxide in a gaseous mixture of hydrogen and carbon monoxide used for the hydroformylation is generally within a range of 1/5 to 5/1 as an inlet gaseous ratio. In addition, a small amount of gases inactive to the hydroformylation, for example, nitrogen and argon, may be present in the reaction atmosphere.

The reaction pressure is generally within a range of 30 to 250 atmospheric pressure. The reaction pressure is preferably within a range of 30 to 200 atmospheric pressure, more preferably within a range of 30 to 150 atmospheric pressure, in order to attain higher reaction rate and selectivity to the branched aldehyde represented by the formula (1) and to carry out the reaction industrially advantageously from the viewpoint of equipment and easy operation.

The hydroformylation according to the present invention can be carried out in a known reaction apparatus such as stirring-type reaction vessel or bubble-column type reaction vessel. The hydroformylation can be carried out in a batchwise manner or in a continuous manner.

The hydroformylation can be carried out either in the absence of a solvent or in the presence of an appropriate solvent. Such solvent includes, for example, saturated aliphatic hydrocarbons such as hexane, heptane and octane; aromatic hydrocarbons such as benzene, toluene and xylene; ethers such as diethyl ether, tetraethylene glycol dimethyl ether, tetrahydrofuran and dioxane; and halogenated hydrocarbons such as dichloromethane. The solvent may be used singly or in combination. The solvent is preferably used in an amount that does not suppress the volumeric efficiency of the hydroformylation.

According to the hydroformylation of the present invention, the linear aldehyde represented by the formula (3) is produced, other than the objective branched aldehyde represented by the formula (1). The ratio of the two, namely the ratio of the branched aldehyde represented by the formula (1) to the linear aldehyde represented by the formula (3) (abbreviated as "ratio i/n" hereinafter), is generally 1.5 or more under the reaction pressure of 200 atm, which is lower than that of the conventional method. Thus, a product containing a higher content of the branched aldehyde represented by the formula (1) can be obtained. If necessary, the branched aldehyde represented by the formula (1) can be separated from the linear aldehyde represented by the formula (3), by known means such as distillation.

The branched aldehyde represented by the formula (1) wherein X is cyano group or an alkoxycarbonyl group is a novel compound. Examples of such novel compound include 1-cyano-2-formylpropyl acetate, 1-cyano-2-formylpropyl propionate, 1-cyano-2-formylpropyl butyrate, 1-cyano-2-formylpropyl isobutyrate, 1-cyano-2-formylpropyl valerate, 1-cyano-2-formylpropyl hexanoate, 1-cyano-2-formylpropyl heptanoate, 1-methoxycarbonyl-2-formylpropyl acetate, 1-methoxycarbonyl-2-formylpropyl propionate, 1-methoxycarbonyl-2-formylpropyl butyrate, 1-methoxycarbonyl-2-formylpropyl isobutyrate, 1-methoxycarbonyl-2-formylpropyl valerate, 1-methoxycarbonyl-2-formylpropyl hexanoate, 1-methoxycarbonyl-2-formylpropyl heptanoate, 1-ethoxycarbonyl-2-formylpropyl acetate, 1-ethoxycarbonyl-2-formylpropyl propionate, 1-propoxycarbonyl-2-formylpropyl acetate, 1-propoxycarbonyl-2-formylpropyl propionate, 1-butoxycarbonyl-2-formylpropyl acetate, 1-butoxycarbonyl-2-formylpropyl propionate, 1-t-butoxycarbonyl-2-formylpropyl acetate, 1-t-butoxycarbonyl-2-formylpropyl propionate, 1-benzyloxycarbonyl-2-formylpropyl acetate and 1-benzyloxycarbonyl-2-formylpropyl propionate.

The reaction solution obtained by the hydroformylation according to the present invention can be used, as it is, for the starting meterials of the next reaction. Or, if desired, a fraction containing the branched aldehyde represented by the formula (1) obtained by vaporization of the reaction solution under reduced pressure, can be used for the next reaction.

The whole or a part of the rhodium compound in the residuals after the vaporization of the reaction solution can be recycled for the hydroformylation.

Furthermore, the branched aldehyde represented by the formula (1) can be isolated from the fraction containing the same through purification by known means such as distillation.

The branched aldehyde represented by the formula (1) can be converted, by the elimination of a carboxylic acid (YOH; wherein Y is the same as defined above), into an $\alpha$, $\beta$-unsaturated aldehyde represented by the formula (4);

(4)

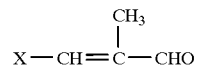

wherein X is the same as defined above. The elimination of a carboxylic acid from the branched aldehyde represented by the formula (1) is generally carried out by heating the branched aldehyde in the presence or absence of a catalyst. From the viewpoint of reaction rate, the elimination is preferably carried out in the presence of a catalyst. Examples of the catalyst include acidic catalyst such as sulfuric acid, hydrochloric acid, phosphoric acid, p-toluenesulfonic acid, alumina, silica alumina, activated clay and ion-exchange resin; and basic catalyst such as sodium hydroxide, potassium hydroxide, triethylamine and triethanolamine. The catalyst is used generally at an amount of 0.01% by weight or more, preferably at an amount of 0.05 to 5% by weight, based on the reaction solution for the elimination.

The elimination of a carboxylic acid from the branched aldehyde represented by the formula (1) is carried out preferably at a temperature of 30° C. or more, more preferably at a temperature within a range of 60 to 120° C.

The elimination is generally carried out at a pressure within a range of 0.001 to 10 atmospheric pressure (absolute pressure). If desired, the elimination is carried out under reduced pressure to remove the formed carboxylic acid from the reaction solution.

The elimination can be carried out either in the absence of a solvent or in the presence of an appropriate solvent. Examples of such solvent include, for example, aromatic hydrocarbons such as benzene, toluene and xylene; aliphatic hydrocarbons such as hexane and heptane; ethers such as diethyl ether, tetraethylene glycol dimethyl ether, tetrahydrofuran and dioxane; and halogenated hydrocarbons such as dichloromethane. These solvents may be used singly or in combination. The solvent is preferably used in an amount that does not suppress the volumeric efficiency of the elimination.

The elimination can be carried out in a stirring-type reaction vessel with the catalyst dissolved or suspended in the reaction solution, or in a fixed-bed type reaction vessel charged with a carried-type catalyst. Also, the elimination can be carried out in a batch-wise manner or in a continuous manner.

After the reaction is completed, the resulting α, β-unsaturated aldehyde represented by the formula (4) can be isolated by a known process, for example, comprising neutralizing the formed carboxylic acid, if necessary, and distilling the reaction mixture.

The thus obtained, β-unsaturated aldehyde represented by the formula (4) can be purified by known method such as distillation under reduced pressure and column chromatography.

Other features of the present invention will become apparent in the course of the following descriptions of exemplary embodiments which are given for illustration of the present invention and are not intended to be limiting thereof.

EXAMPLES

Example 1

An autoclave equipped with a gas inlet, a sampling port and an electromagnetic stirrer and having an internal volume of 300 ml, was charged with 90 ml (194.8 g, 0.55 mol) of 3,4-diacetoxy-1-butene and a solution of 2.58 mg (0.01 mmol) of rhodium dicarbonyl acetylacetonate and 323 mg (0.5 mmol) of tris(2,4-di-t-butylphenyl) phosphite in 10 ml of toluene under nitrogen while avoiding their contact with air. Then the atmosphere inside the autoclave was replaced with a gaseous mixture of hydrogen and carbon monoxide at a molar ratio of 1/1. The pressure inside the autoclave was adjusted to 100 atmospheric pressure (gauze pressure) with the same gaseous mixture and the temperature inside the autoclave was raised to 60° C. The hydroformylation was effected for 8 hours at 60° C. while maintaining the pressure inside the autoclave at 100 atmospheric pressure (gauze pressure) with the gaseous mixture of hydrogen and carbon monoxide at a molar ratio of 1/1.

Analysis of the reaction solution with gas chromatography [column: G-300, 1.2 mm Φ×20 m, manufactured by Chemicals Inspection and Testing Institute, Japan; column temperature: raised to 200° C. from 70° C. (rate of temperature rise: 10° C./min)] showed that the conversion of the 3,4-diacetoxy-1-butene was 89% and the selectivity the hydroformylated product was 99%. The analysis also showed that the reaction solution contained 72.5 g (0.36 mol) of 1,2-diacetoxy-3-formylbutane and 25.4 g (0.13 mol) of 4,5-diacetoxypentanal at the ratio i/n of 2.8 (=74/26).

Example 2

The general procedures of Example 1 were repeated except that the amount of tris(2,4-di-t-butylphenyl) phosphite, the reaction temperature and the reaction time were changed to 129 mg (0.5 mmol), 80° C. and 2 hours, respectively. Analysis of the reaction solution with gas chromatography under the same conditions of Example 1 showed that the conversion of the 3,4-diacetoxy-1-butene was 92%, the selectivity to the hydroformylated product was 99% and the ratio i/n was of 2.0 (=67/33).

Example 3

The general procedures of Example 1 were repeated except that the reaction pressure, the reaction temperature and the reaction time were changed to 90 atmospheric pressure, 80° C. and 2 hours, respectively. Analysis of the reaction solution with gas chromatography under the same conditions of Example 1 showed that the conversion of the 3,4-diacetoxy-1-butene was 99%, the selectivity to the hydroformylated product was 98% and the ratio i/n was 2.2 (=69/31).

Example 4

The general procedures of Example 1 were repeated except that 155 mg (0. 5 mmol) of triphenyl phosphite was used instead of 323 mg of tris (2,4-di-t-butylphenyl) phosphite and that the reaction pressure, the reaction temperaure and the reaction time were changed to 90 atmospheric pressure, 80° C. and 4 hours, respectively. Analysis of the reaction solution with gas chromatography under the same conditions of Example 1 showed that the conversion of the 3,4-diacetoxy-1-butene was 71%, the selectivity to the hydroformylated product was 98% and the ratio i/n was 2.2 (=69/31).

Comparative Example 1

The general procedures of Example 4 were repeated except that 131 mg (0.5 mmol) of triphenylphosphine was used instead of 155 mg of triphenyl phosphite. Analysis of the reaction solution with gas chromatography under the same conditions of Example 1 showed that the conversion of the 3,4-diacetoxy-1-butene was 11%, the selectivity to the hydroformylated product was 98% and the ratio i/n was 1.1 (=53/47).

Comparative Example 2

The general procedures of Example 4 were repeated except that 125 mg (0.5 mmol) of tri-n-butyl phosphite was used instead of 155 mg of triphenyl phosphite. Analysis of the reaction solution with gas chromatography under the same conditions of Example 1 showed that the conversion of the 3,4-diacetoxy-1-butene was 19%, the selectivity to the hydroformylated product was 98% and the ratio i/n was 1.2 (=54/46).

Example 5

An autoclave equipped with a gas inlet, a sampling port and an electromagnetic stirrer and having an internal volume of 300 ml, was charged with 50 ml (52.7 g, 0.306 mol) of 3,4-diacetoxy-1-butene and a solution of 2.58 mg of rhodium dicarbonyl acetylacetonate and 140 mg (0.5 mmol)

of tricyclohexylphosphine in 50 ml of toluene under nitrogen while avoiding their contact with air. Then, the atmosphere inside the autoclave was replaced with a gaseous mixture of hydrogen and carbon monoxide at a molar ratio of 1/1. The pressure inside the autoclave was adjusted to 90 atmospheric pressure (gauze pressure) with the same gaseous mixture and the temperature inside the autoclave was raised to 80° C. The hydroformylation was effected for 2 hours at 80° C. while maintaining the pressure inside the autoclave at 90 atmospheric pressure (gauze pressure) with the gaseous mixture of hydrogen and carbon monoxide at a molar ratio of 1/1. Analysis of the reaction solution with gas chromatography under the same conditions of Example 1 showed that the conversion of the 3,4-diacetoxy-1-butene was 44% and the selectivity to the hydroformylated product was 99%. The anaysis also showed that the reaction solution contained 13.55 g (67 mmol) of 1,2-diacetoxy-3-formylbutane and 8.29 g (41 mmol) of 4,5-diacetoxypentanal and 3.55 g (25 mmol) of 3-methyl-4-oxo-2-butenyl acetate which was formed by the elimination of acetic acid from 1,2-diacetoxy-3-formylbutane. The ratio i/n was 2.2 (=69/31), wherein 3-methyl-oxo-2-butenyl acetate was calculated as 1,2-diacetoxy-3-formylbutane.

Comparative Example 3

The general procedures of Example 5 were repeated except that tricyclohexylphosphine was not used. Analysis of the reaction solution with gas chromatography under the same conditions of Example 1 showed that the conversion of the 3,4-diacetoxy-1-butene was 41%, the selectivity to the hydroformylated product was 95% and the ratio i/n was 0.67 (=40/60).

Example 6

An autoclave equipped with a gas inlet, a sampling port and an electromagnetic stirrer and having an internal volume of 300 ml, was charged with 30 ml (30.8 g, 0.246 mol) of 1-cyano-2-propenyl acetate and a solution of 3.9 mg (0.015 mmol) of rhodium dicarbonyl acetylacetonate and 485 mg (0.75 mmol) of tris(2,4-di-t-butylphenyl) phosphite in 120 ml of toluene under nitrogen while avoiding their contact with air. Then, the atmosphere inside the autoclave was replaced with a gaseous mixture of hydrogen and carbon monoxide at a molar ratio of 1/1. The pressure inside the autoclave was adjusted to 90 atmospheric pressure with the same gaseous mixture and the temperature inside the autoclave was raised to 80° C. The hydroformylation was effected for 2 hours at 80° C. while maintaining the pressure inside the autoclave at 90 atmospheric pressure (gauze pressure) with a gaseous mixture of hydrogen and carbon monoxide at a molar ratio of 1/1. Analysis of the reaction solution with gas chromatography [column: G-300, 1.2 mmΦ×20 m; column temperature: raised to 200° C. from 100 ° C. (rate of temperature rise: 10° C./min)] showed that the conversion of the 1-cyano-2-propenyl acetate was 99% and the selectivity to the hydroformylated product was 98%. The analysis also showed that the reaction solution contained 31.1 g (201 mmol) of 1-cyano-2-formylpropyl acetate and 5.9 g (38 mmol) of 1-cyano-4-oxobutyl acetate, a linear aldeyde. The ratio i/n was 5.3.

Distillation of the reaction solution under reduced pressure gave 30.7 g of 1-cyano-2-formylpropyl aceate as a fraction with a boiling point of 75° C. to 81° C./1 mmHg (purity: 91%). The obtained 1-cyano-2-formylpropyl acetate was a mixture of two diastereomers (threo isomer and erythro isomer). Properties of the product are shown below.

Diastereomer (1)
$^1$H-NMR(270 MHz, CDCl$_3$, TMS) δ(ppm): 1.39(d, 3H, J=6.8 Hz), 2.14(s, 3H), 3.03(dq, 1H, J =6.0 Hz, 6.8 Hz), 5.66(d, 1H, J=6.0 Hz), 9.67(s, 1H)

Diastereomer (2)
$^1$H-NMR(270 MHz, CDCl$_3$, TMS) δ(ppm): 1.43(d, 3H, J=6.7 Hz), 2.14(s, 3H), 2.95(dq, 1H, J=3.8 Hz, 6.7 Hz), 5.70(d, 1H, J=3.8 Hz), 9.67(s, 1H)

The ratio of diastereomers, diastereomer (1)/diastereomer (2), was about 50/50, as calculated on the basis of $^1$H-NMR spectrum.

In addition, 6.4 g of 1-cyano-4-oxobutyl acetate was obtained as a fraction with a boiling point of 98° C. to 102° C./1 mmHg (purity: 81%) by the above distillation. Propeties of the compound are shown below. $^1$H-NMR(270 MHz, CDCl$_3$, TMS) δ(ppm): 2.15(s, 3H), 2.22–2.30(m, 2H), 2.73–2.78(m, 2H), 5.41(t, 1H, J=5.8 Hz), 9.81(s, 1H)

Example 7

An autoclave equipped with a gas inlet, a sampling port and an electromagnetic stirrer and having an internal volume of 300 ml, was charged with 30 ml (31.8 g, 0.201 mol) of 1-methoxycarbonyl-2-propenyl acetate and a solution of 3.9 mg of rhodium dicarbonylacetylacetonate and 485 mg of tris(2,4-di-t-butylphenyl) phosphite in 120 ml of toluene under nitrogen while avoiding their contact with air. Then, the atmosphere inside the autoclave was replaced with a gaseous mixture of hydrogen and carbon monoxide at a molar ratio of 1/1. The pressure inside the autoclave was adjusted to 90 atmospheric pressure with the same gaseous mixture and the temperature inside the autoclave was raised to 80° C. The hydroformylation was effected for 2 hours at 80° C. while maintaining the pressure inside the autoclave at 90 atmospheric pressure (gauze pressure) with a gaseous mixture of hydrogen and carbon monoxide ata molar ratio of 1/1. Analysis of the reaction solution with gas chromatography under the same conditions of Example 6 showed that the conversion of the 1-methoxycarbonyl-2-propenyl acetate was 99% and the selectivity to the hydroformylated product was 98%. The analysis also showed that the reaction solution contained 28.2 g (150 mmol) of 1-methoxycarbonyl-2-formylpropyl acetate and 8.4 g (44 mmol) of 1-methoxycarbonyl-4-oxobutyl acetate, a linear aldeyde. The ratio i/n was 3.4.

Distillation of the reaction solution under reduced pressure gave 28.5 g of 1-methoxycarbonyl-2-formylpropyl aceate as a fraction with a boiling point of 87° C. to 89° C./1 mmHg (purity: 89%). The obtained 1-methoxycarbonyl-2-formylpropyl acetate was a mixture of two diastereomers (threo isomer and erythro isomer). Properties of the product are shown below.

Diastereomer (1)
$^1$H-NMR(270 MHz, CDCl$_3$, TMS) δ(ppm): 1.21(d, 3H, J=6.5 Hz), 2.16(s, 3H), 2.96–2.99(m, 1H), 3.78(s, 3H), 5.38(d, 1H, J=4.2 Hz), 9.69(s, 1H)

Diastereomer (2)
$^1$H-NMR(270 MHz, CDCl$_3$, TMS) δ(ppm): 1.22(d, 3H, J=6.5 Hz), 2.13(s, 3H), 2.96–2.99(m, 1H), 3.79(s, 3H), 5.59(d, 1H, J=3.0 Hz), 9.67(s, 1H)

The ratio of diastereomers, diastereomer (1)/diastereomer (2), was about 59/41, as calculated on the basis of $^1$H-NMR spectrum.

In addition, 8.4 g of 1-methoxycarbonyl-4-oxobutyl acetate was obtained as a fraction with a boiling point of 107° C. to 108° C./1 mmHg (purity: 90%) by the above distillation. Properties of the compound are shown below.

$^1$H-NMR(270 MHz, CDCl$_3$, TMS) δ(ppm): 2.13(s, 3H), 2.16–2.27(m, 2H), 2.58–2.65(m, 2H), 3.75(s, 3H), 5.04(dd, 1H, J=4.5 Hz, 6.7 Hz), 9.78(s, 1H)

Example 8

The general procedures of Example 7 were repeated except that the amount of rhodium dicarbonyl acetylacetonate and the reaction temperature were changed to 7.8 mg and 60° C., respectively. Analysis of the reaction solution with gas chromatography under the same conditions of Example 6 showed that the conversion of the 1-methoxycarbonyl-2-formylpropyl acetate was 99% and the selectivity to the hydroformylated product was 98%. The analysis also showed that the reaction solution contained 31.1 g (165 mmol) of 1-methoxycarbonyl-2-formylpropyl acetate and 5.5 g (29 mmol) of 1-methoxycarbonyl-4-oxobutyl acetate. The ratio i/n was 5.7.

Reference Example 1

A three-necked flask of an internal volume of 200 ml was charged with 100 g of the reaction solution obtained in the Example 1 [containing 62 g (0.31 mol) of 1,2-diacetoxy-3-formylbutane] and 0.5 g of p-toluenesulfonic acid monohydrate under nitrogen. Then the resulting mixture was heated to 80° C. and stirred for 5 hours under atmospheric pressure. The resulting reaction mixture was cooled to room temperature and neutralized with 0.8 g of triethanolamine. Analysis of the reaction solution with gas chromatography under the same conditions of Example 1 showed that 41 g (0.29 mol) of 3-methyl-4-oxo-2-butenyl acetate was formed. Distillation of the reaction solution under reduced pressure gave 35 g of 3-methyl-4-oxo-2-butenyl acetate (boiling point: 121° C./30 Torr).

Reference Example 2

A three-necked flask of an internal volume of 50 ml was charged with 15 g of the reaction solution obtained in the Example 6 [containing 13.6 g (87.7 mmol) of 1-cyano-2-formylpropyl acetate] and 0.15 g of p-toluenesulfonic acid monohydrate under nitrogen. Then the-resulting mixture was heated to 100° C. and stirred for 3 hours under atmospheric pressure. The reaction mixture was cooled to room temperature and neutralized with 0.2 g of triethanolamine. Analysis of the resulting reaction mixture with gas chromatography under the same conditions of Example 6 showed that 7.7 g (81 mmol) of 3-methyl-4-oxo-2-butenenitrile was formed. The conversion of the 1-cyano-2-formylpropyl aceate was 100% and the selectivity to the 3-methyl-4-oxo-2-butenenitrile was 92%.

Distillation of the reaction mixture under reduced pressure gave 7.3 g of 3-methyl-4-oxo-2-butenenitrile (boiling point: 75° C. to 81° C./1 mmHg, purity: 95%).

Reference Example 3

A three-necked flask of an internal volume of 50 ml was charged with 20 g of the reaction solution obtained in Example 7 [containing 18.0 g (95.7 mmol) of 1-methoxycarbonyl-2-formypropyl acetate] and 0.5 g of triethanolamine under nitrogen. Then the resulting mixture was heated to 100° C. and stirred for 3 hours under atmospheric pressure. The reaction mixture was cooled to room temperature. Analysis of the reaction mixture with gas chromatography under the same conditions of Example 6 showed that 10.9 g (85.2 mmol) of methyl 3-methyl-4-oxo-2-butenoate was formed. The conversion of the 1-methoxycarbonyl-2-formylpropyl aceate was 100% and the selectivity to the methyl 3-methyl-4-oxo-2-butenoate was 90%.

Distillation of the reaction mixture under reduced pressure gave 8.9 g of methyl 3-methyl-4-oxo-2-butenoate (boiling point: 45° C. to 46° C./3 mmHg, purity: 99%)

Reference Example 4

The general procedures of the Reference Example 3 were repeated except that 50 g of the reaction solution obtained in Example 8 [containing 11.1 g of 1-methoxycarbonyl-2-formylpropyl acetate] was used instead of 20 g of the reaction solution obtained in Example 7. Analysis of the reaction mixture with gas chromatography under the same conditions of Example 6 showed that 7.0 g of methyl 3-methyl-4-oxo-2-butenoate was formed. The conversion of the 3-methoxycarbonyl-2-formylpropyl acetate was 100% and the selectivity to the methyl 3-methyl-4-oxo-2-butenoate was 93%.

Obviously, numerous modifications and variations are possible in light of the above teachings. It is therefore to be understood that within the scope of the appended claims, the present invention may be practiced otherwise than as specifically described herein.

What is claimed is:

1. A process for producing a branched aldehyde represented by the formula;

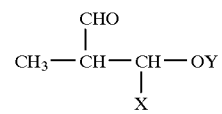

wherein Y represents an acyl group of two or more carbon atoms; and X represents an acyloxymethyl group represented by $-CH_2OY'$, cyano group or an alkoxycarbonyl group and wherein Y' represents an acyl group of two or more carbon atoms, comprising subjecting an olefinic compound represented by the following formula:

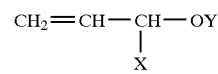

wherein Y and X are the same as defined above, to the reaction with hydrogen and carbon monoxide in the presence of a rhodium compound and a tertiary organic phosphite with an electronic parameter (υ-value) of 2080 to 2090 $cm^{-1}$ and with a steric parameter (θ-value) of 150 to 180°.

2. A process according to claim 1, wherein the concentration of the rhodium compound in the reaction solution is 0.01 to 0.25 mg atom/liter on a rhodium atom basis and the concentration of the tertiary organic phosphite in the reaction solution is 2 to 10 millimoles/liter.

3. A process according to claim 1, wherein the concentration of the rhodium compound in the reaction solution is 0.01 to 0.25 mg atom/liter on a rhodium atom basis and the concentration of the tertiary organic phosphite in the reaction solution is 2 to 10 millimoles/liter.

4. A process for producing α, β-unsaturated aldehyde represented by the following formula;

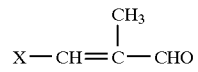

(wherein X represents an acyloxymethyl group represented by $-CH_2OY'$ (wherein Y' represents an acyl group of two or more carbon atoms), cyano group or an alkoxycarbonyl group), comprising eliminating a carboxylic acid (Y-OH) from a branched aldehyde represented by the formula;

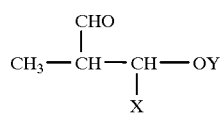

(wherein Y is an acyl group of two or more carbon atoms; and X is the same as defined above) which is produced by subjecting an olefinic compound represented by the following formula;

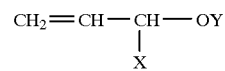

(wherein X and Y are as defined above), to the reaction with hydrogen and carbon monoxide in the presence of a rhodium compound and a tertiary organic phosphite with an electronic parameter ($\upsilon$-value) of 2080 to 2090 cm$^{-1}$ and with a steric parameter ($\theta$-value) of 150 to 180°.

* * * * *